United States Patent [19]

Hurd

[11] Patent Number: 5,472,439
[45] Date of Patent: Dec. 5, 1995

[54] ENDOSCOPIC SURGICAL INSTRUMENT WITH ROTATABLE INNER SHAFT

[75] Inventor: Stanley M. Hurd, Hamden, Conn.

[73] Assignee: American Cyanamid Company, Wayne, N.J.

[21] Appl. No.: 132,724

[22] Filed: Oct. 6, 1993

[51] Int. Cl.⁶ ................................................ A61B 17/00
[52] U.S. Cl. ............................ 606/1; 606/205; 606/71; 606/174
[58] Field of Search ........................ 606/205, 206, 606/207, 208, 170, 171, 174, 47, 52, 51, 142, 148, 113, 46, 1; 128/751

[56] References Cited

U.S. PATENT DOCUMENTS

| | | | |
|---|---|---|---|
| 4,258,716 | 3/1981 | Sutherland | 606/174 X |
| 4,499,899 | 2/1985 | Lyons, III . | |
| 4,590,936 | 5/1986 | Straub et al. . | |
| 4,601,290 | 7/1986 | Effron et al. . | |
| 4,848,338 | 7/1989 | De Satnick et al. | 606/171 X |
| 4,986,825 | 1/1991 | Bays et al. . | |
| 5,171,256 | 12/1992 | Smith et al. . | |
| 5,171,257 | 12/1992 | Ferzli . | |
| 5,171,258 | 12/1992 | Bales et al. . | |
| 5,176,699 | 1/1993 | Markham . | |
| 5,196,003 | 3/1993 | Bilweis . | |
| 5,196,023 | 3/1993 | Martin . | |
| 5,203,785 | 4/1993 | Slater . | |
| 5,222,973 | 6/1993 | Sharpe et al. . | |
| 5,281,220 | 1/1994 | Blake, III | 606/205 X |
| 5,282,806 | 2/1994 | Haber et al. | 606/205 X |

FOREIGN PATENT DOCUMENTS

| | | |
|---|---|---|
| 0537574 | 4/1993 | European Pat. Off. . |
| 0543107 | 5/1993 | European Pat. Off. . |
| 0541930 | 5/1993 | European Pat. Off. . |
| 0546264 | 6/1993 | European Pat. Off. . |
| 0555105 | 8/1993 | European Pat. Off. . |
| WO9301754 | 2/1993 | WIPO . |

*Primary Examiner*—Peter A. Aschenbrenner
*Attorney, Agent, or Firm*—Charles F. Costello, Jr.; Gene B. Kartchner

[57] ABSTRACT

A reusable endoscopic surgical instrument includes a handle assembly attached to a slender shaft assembly. The shaft assembly includes inner and outer shafts, with the inner shaft being rotatable by operation of the handle assembly to rotate a surgical tool operably connected to the distal end of a pushrod disposed within the inner shaft. The handle assembly includes first actuating mechanism for actuating the pushrod to operate the surgical tool and a second actuating mechanism for rotating the inner shaft. The outer shaft is axially slidable with respect to the inner shaft to cover a flush port system in the handle assembly for cleaning and improved sterilizability of the instrument.

30 Claims, 6 Drawing Sheets

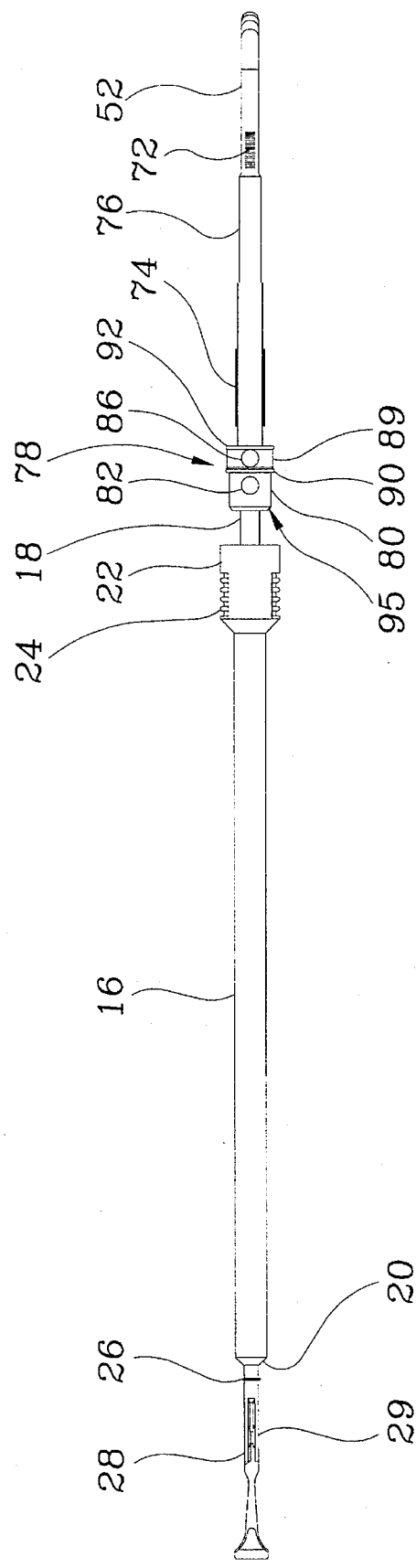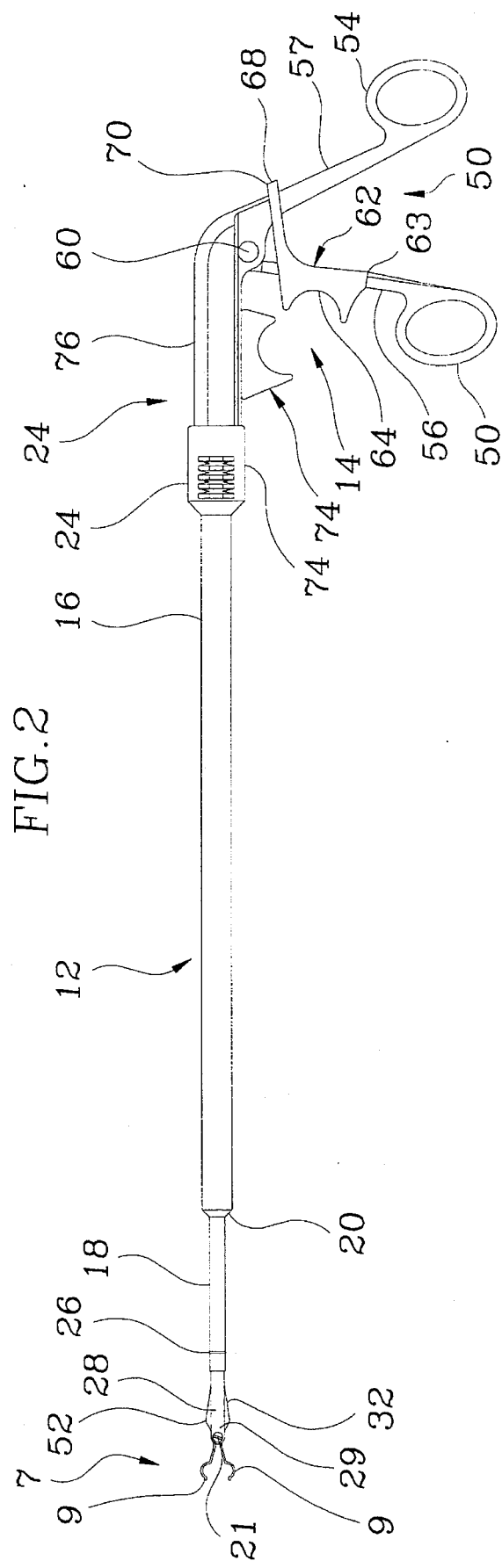
FIG. 2
FIG. 1

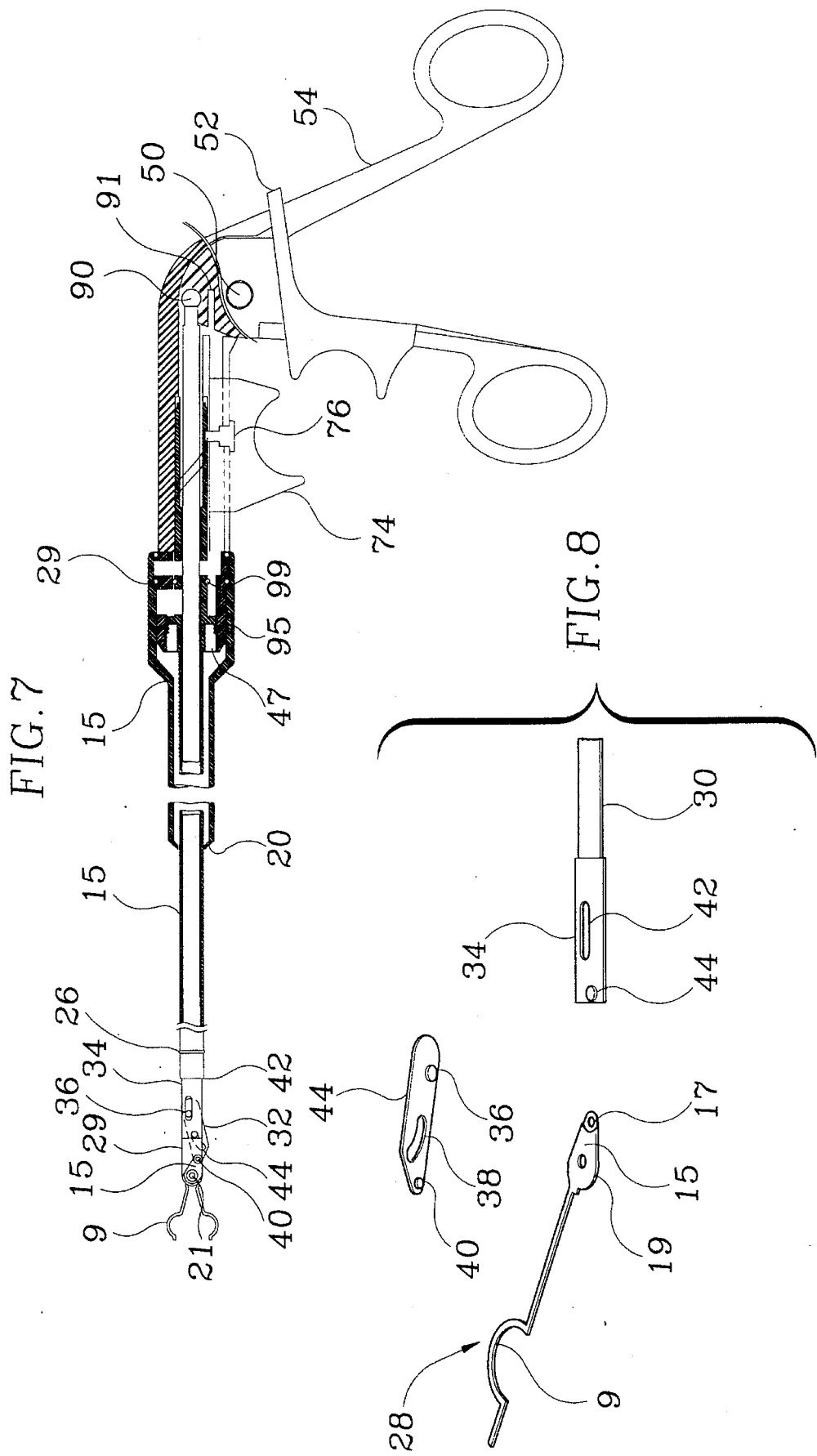

ENDOSCOPIC SURGICAL INSTRUMENT WITH ROTATABLE INNER SHAFT

BACKGROUND OF THE INVENTION

1. Field of the Invention

The invention relates generally to a medical instrument for use in endoscopic surgical procedures, and more particularly to an endoscopic surgical instrument capable of rotatably manipulating an attached surgical tool.

The burgeoning field of endoscopic surgery utilizes surgical instruments with slender barrel portions for entering cannulas placed in small incisions or wounds in the patient's body. The advantages of Endoscopic surgery over conventional open procedure surgery are due in large part to elimination of the need to make large incisions in the patient, and include reduced patient trauma, quicker recovery time and a significantly lower chance of infection.

The distal end of the barrel portion of an endoscopic instrument can be provided with a precision surgical tool, such as a pair of jaws or a pair of scissors, for performing various surgical tasks such as gripping tissue or body organs, cutting ligaments, and the like. The surgical tool is actuated by a handle assembly attached to a proximal end of the barrel portion and operated by a surgeon/user.

With the working length of the endoscopic surgical instrument, i.e., the portion of the instrument inserted into the cannula, typically being 12 inches or more, it is desirable to provide the surgeon/user with means to precisely maneuver the surgical tool at the distal end after the instrument is inserted into the patient's body. Moreover, when an endoscopic surgical instrument is inserted into an insufflated body cavity, it is desirable to create an airtight seal between the cannula and the barrel portion. To preserve this seal, relative movement between the barrel portion and the cannula should be kept to a minimum.

2. Description of the Prior Art

A conventional endoscopic surgical instrument typically includes a handle assembly and a slender, elongated barrel portion attached at its proximal end to the handle portion. A distal end of the barrel portion has a surgical tool, or attachment, such as a pair of gripping jaws for gripping tissue or other internal body parts. The slender barrel portion is inserted through the cannula in the patient's body and the handle portion is operated by the surgeon/user to mechanically operate the surgical tool.

Endoscopic surgical instruments have advanced mechanically to the point where they are capable of orienting the surgical tool, that is, angularly rotating the tool about the longitudinal axis of the surgical instrument, to properly align the surgical tool while allowing the surgeon/user to operate the handle assembly in a normal, comfortable position. For example, U.S. Pat. No. 4,258,716 is directed to an endoscopic instrument that includes a pair of rotary cutting scissors at the distal end of a shaft assembly. A first set screw is used to lock a pair of scissor blades in position relative to each other, i.e, regulate the blade opening, and a second set screw locks the set of blades in a set angular position with respect to the longitudinal direction of the shaft assembly. However, the set screws must be tightened and the adjustments made before the endoscopic instrument is inserted through the cannula.

An improved endoscopic surgical instrument is disclosed in European Patent Application No. 543,107, published May 26, 1993. The instrument features a handle assembly with a knob that can be rotated by the surgeon/user to rotate the entire elongated body assembly and orient a surgical attachment at various angles with respect to the longitudinal axis of the instrument. International Publication No. WO 93/01754, published Feb. 4, 1993, discloses an endoscopic surgical instrument that includes a plug for rotating an outer tube 12 and orienting a clamp-like tip assembly at any desired angle relative to the longitudinal axis of the instrument. However, with these surgical instruments there is a drag force created by relative movement between the rotated outer tube and the cannula. The drag force makes it difficult to rotate the outer tube, and can also compromise the seal between the outer tube and the cannula, leading to pneumoperitoneal loss in the insufflated body cavity.

Accordingly, further improvements in endoscopic surgical instruments capable of angularly orienting a surgical tool are needed. Other desirable improvements include provision of a surgical instrument designed for easy cleaning and sterilization after each use and of a surgical instrument with better overall mechanical performance.

SUMMARY OF THE INVENTION

It is a principal object of the present invention to provide an improved endoscopic surgical instrument.

Accordingly, one object of the invention is to provide an endoscopic surgical instrument insertable through a cannula and capable of easily and precisely orienting a surgical tool connected at its distal end.

It is another object of the invention to provide an endoscopic surgical instrument that can orient the attached surgical tool without disturbing the airtight seal between the shaft assembly and the cannula.

It is yet another object of the invention to provide a reusable endoscopic surgical instrument designed for easy and thorough cleaning and sterilization after each use.

It is a further object of the invention to provide an endoscopic surgical device designed to limit overtravel of the attached surgical tool and provide a linkage assembly with superior strength and reliability for operating the surgical tool.

It is another object of the invention to provide safety mechanisms for restraining rotation of an inner shaft when the surgical instrument is actuated and locking a handle assembly of the surgical instrument in the actuated position.

These and other objects are achieved by an endoscopic surgical instrument in accordance with the present invention, which in one aspect comprises an elongated shaft assembly having an outer hollow shaft and an inner hollow shaft disposed within the outer shaft. A handle assembly is connected to a proximal end of the shaft assembly. In addition, first actuation means operates a surgical attachment connected to a distal end of the shaft assembly, and second actuation means rotates the inner shaft to orient the surgical attachment with respect to an axial direction of the shaft assembly.

In accordance with another aspect of the invention, an endoscopic surgical instrument comprises an elongated shaft assembly including an outer hollow shaft, an inner hollow shaft disposed within the outer shaft, and a pushrod disposed within the inner shaft. A handle assembly is connected to a proximal end of the shaft assembly. The handle assembly includes an actuating mechanism for actuating the pushrod in the axial direction to operate a surgical tool attached at the distal end of the shaft assembly. Means for imparting rotational movement to the inner shaft are also provided.

In accordance with still another aspect of the invention, an endoscopic surgical instrument comprises an elongated shaft assembly including an outer hollow shaft and an inner hollow shaft connected to a hollow barrel cam having a helical groove. A pushrod is disposed within the inner shaft and the barrel cam and is actuated to slide in an axial direction. In addition, a handle assembly is connected to a proximal portion of the shaft assembly, and includes a squeezable handle operably connected to the pushrod and a slide loop mounted on the handle assembly and operably connected to the cam barrel. Linear movement of the slide loop imparts rotational movement to the cam barrel and inner shaft.

In accordance with yet another aspect of the invention, a system including a plurality of flush ports is provided in the handle assembly for receiving cleansing fluid for cleaning and improved sterilizibility of the surgical instrument. A distal flush port receives fluid for flushing the pushrod and surgical tool linkage, and a proximal flush port receives fluid for flushing the cam barrel and the handle assembly.

In accordance with another aspect of the invention, means are provided to restrain rotation of the cam barrel when the handle assembly is actuated.

In accordance with yet another aspect of the invention, a locking mechanism is provided to lock the handle assembly in the actuated position.

In accordance with another aspect of the invention, the handle assembly is designed to prevent overtravel of the surgical tool actuated by operation of the handle assembly.

In accordance with still another aspect of the invention, a rivetless linkage assembly with integrally machined pins is provided at the distal end of the shaft assembly. The integrally machined pins provide greater strength and durability for actuating the attached surgical tool.

These and other objects, aspects, features and advantages of the present invention will become apparent from the following detailed description of the preferred embodiments taken in conjunction with the accompanying drawings.

BRIEF DESCRIPTION OF THE DRAWINGS

FIG. 1 is a side elevational view of an endoscopic surgical instrument in accordance with the present invention;

FIG. 2 is a top plan view of the endoscopic surgical instrument of the present invention;

FIG. 7 is a side elevational view, partly in cross-section, of the endoscopic surgical instrument of the present invention illustrating a linkage assembly at its distal end;

FIG. 8 is an exploded perspective view of the distal end of the endoscopic surgical instrument of the present invention illustrating selected elements of the surgical tool and the linkage assembly;

DESCRIPTION OF THE PREFERRED EMBODIMENTS

Figure 3A:
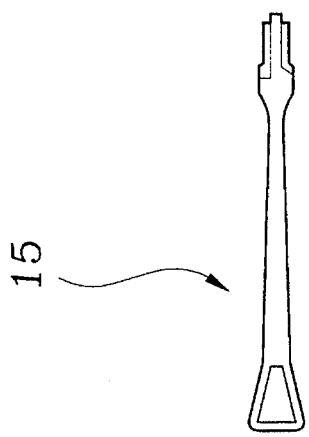
FIGS. 3A and 3B are respectively a top plan view and a side elevational view of one example of a surgical tool attachment that can be connected to the endoscopic surgical instrument of the present invention.

An endoscopic surgical instrument 10 in accordance with the present invention is shown generally in FIG. 1. The main components of the surgical instrument are a slender elongated shaft assembly 12 connected at its proximal end to a handle assembly 14. A surgical tool or attachment 7, such as a pair of jaws 9, is connected to the distal end of the shaft assembly 12. In use, the shaft assembly enters a patient's body through a cannula and the handle assembly is operated by a surgeon/user to maneuver and actuate the surgical tool.

Figure 4A:
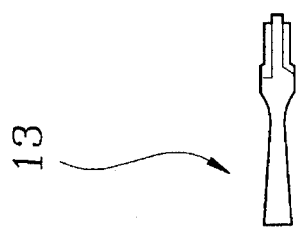
FIGS. 4A and 4B are respectively a top plan view and a side elevation view of a second example of a surgical tool attachment that can be connected to the endoscopic surgical instrument of the present invention.
Figure 5A:
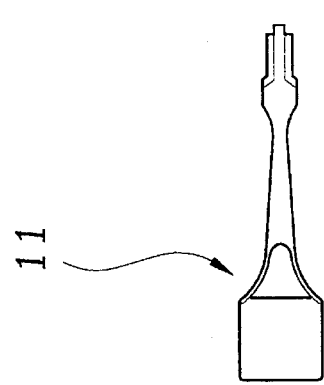
FIGS. 5A and 5B are respectively a top plan view and a side elevational view of a third example of a surgical tool attachment that can be connected to the endoscopic surgical instrument of the present invention.
Figure 3B:
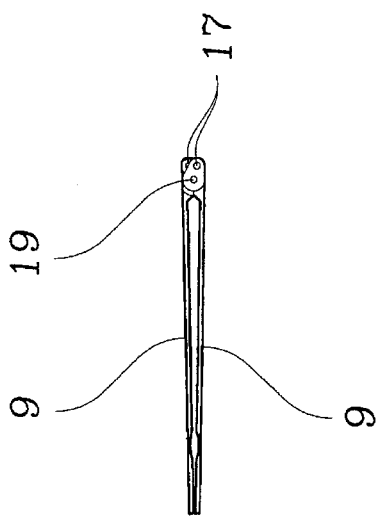
Figure 4B:
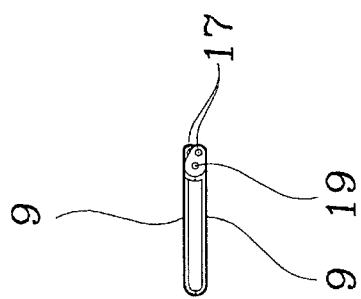
Figure 5B:
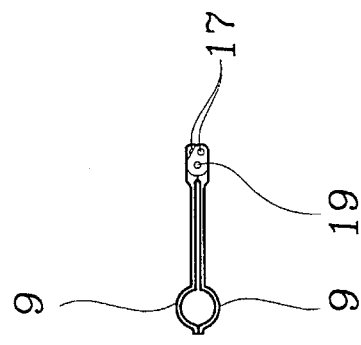

A number of different surgical tools can readily be used with the endoscopic surgical instrument of the present invention depending upon the surgical task to be performed. For example, a pair of atraumatic Babcock jaws 11 are shown in FIGS. 3A and 3B and are ideally suited for gripping tissue. Other tissue gripping attachments that can be used with the subject invention include a pair of Allis jaws 13 as shown in FIGS. 4A and 4B and a pair of Pennington jaws 15 as shown in FIGS. 5A and 5B. In accordance with the subject invention, the jaws are opened and closed for gripping tissue, for example, and can be oriented by rotation about a longitudinal axis of the shaft assembly by operating the handle assembly in a manner described below. Still other surgical tools, such as scissors, dissectors, suturing needle holders, and the like, can be attached to and operated by the endoscopic surgical instrument of the present invention. Indeed, it will be appreciated from the description below that the linkage mechanism of the present invention will work equally well with any two-member surgical tool that operates in a scissors-like manner. However, for convenience the invention will be described with reference to the tissue-gripping jaw tool of FIGS. 1 and 2.

Figure 6:
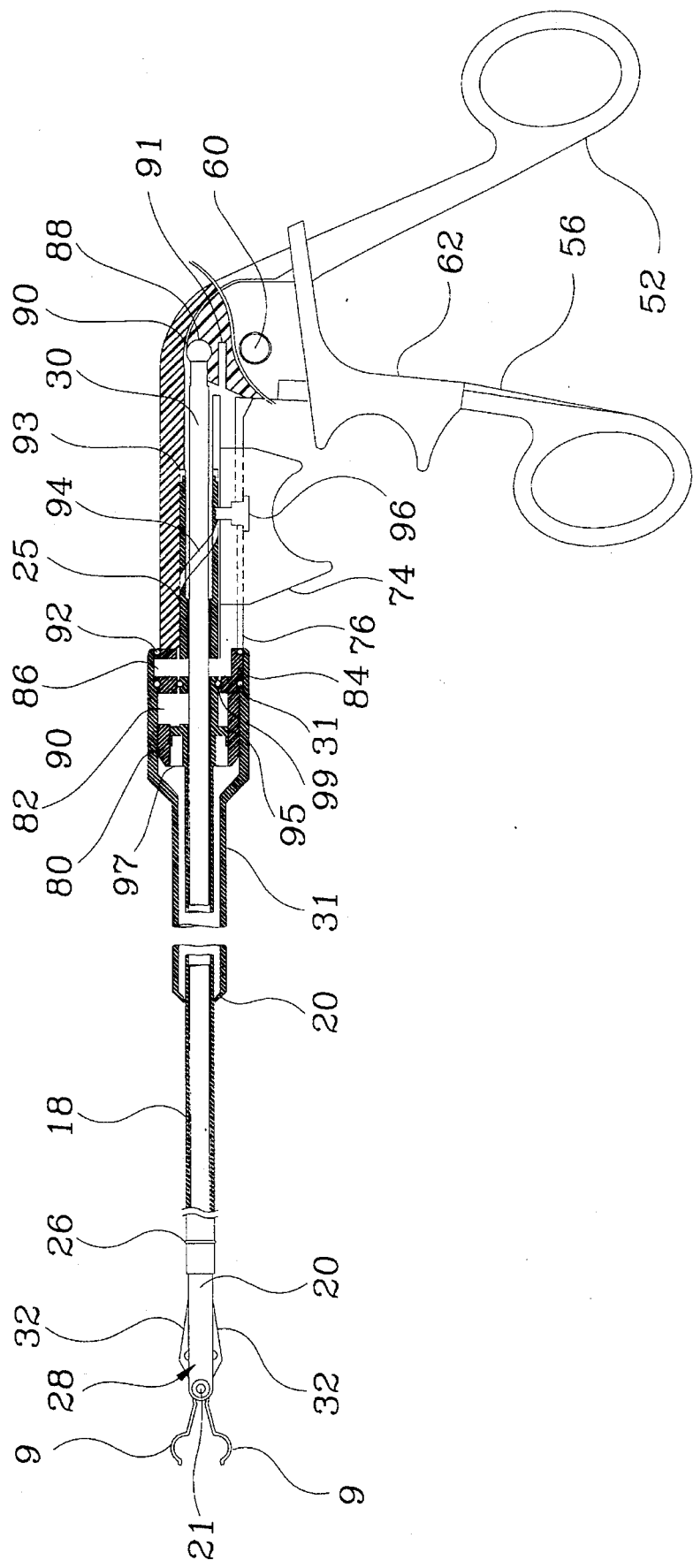
FIG. 6 is a side elevational view, partly in cross-section, of the endoscopic surgical instrument of the present invention with an attached surgical tool in the open-jaw position.
Figure 10:
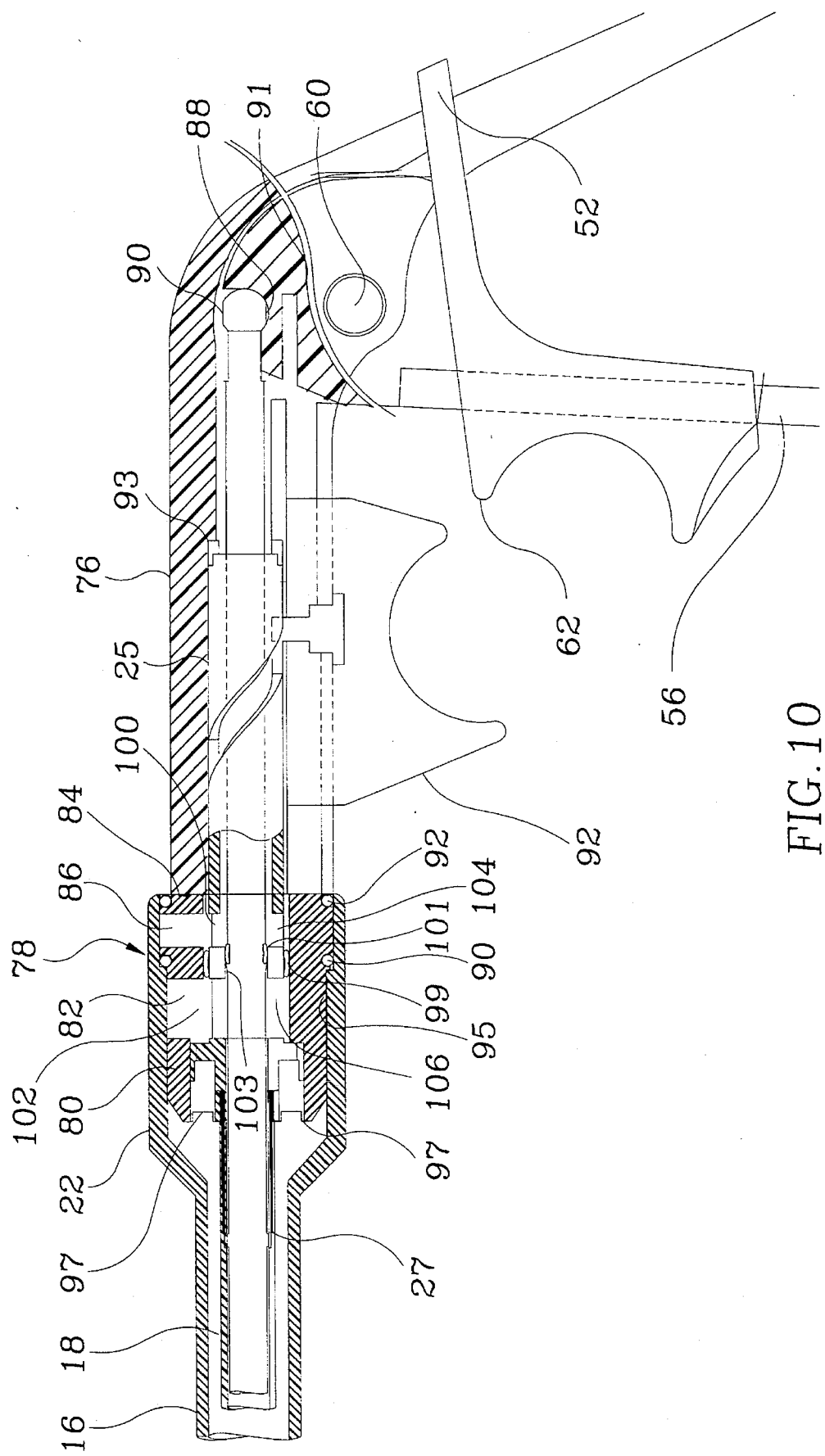
FIG. 10 is a detailed partial cross-sectional view of the endoscopic surgical instrument of the present invention.

The shaft assembly 12 will now be described in detail with reference primarily to FIGS. 1 and 6. In particular, this assembly includes an outer hollow shaft 16 and an elongated inner hollow shaft 18 disposed within the outer shaft for relative axial reciprocal sliding movement. The outer hollow shaft 16 is preferably fabricated from a high temperature-resistant plastic and may be, for example, 10 mm in outside diameter to provide an airtight seal when inserted within a conventionally and complementary sized cannula. The outer shaft has a tapered front end 20 and an enlarged-diameter rear end 22. The rear end is formed with an interior stepped portion 31 and exterior gripping surfaces 24 that fit over a distal portion of the handle assembly. The outer shaft is normally disposed in its rearward position as shown in FIGS. 1 and 6 when the surgical instrument is in use to cover a multiple flush port system in the handle assembly that will be described in detail below. However, the outer shaft can slide forwardly over the inner shaft to a position shown in FIG. 2 to expose dual flush ports 82 and 86 in the handle assembly for cleaning the surgical instrument. A stop 26 on the inner shaft 18 limits forward movement of the outer shaft. The inner shaft 18 may preferably be approximately 5 mm in diameter and be made of, for example, a rounded stainless steel shaft covered with a thin layer of hard resin plastic. As best seen in FIG. 10, the inner shaft 18 is connected at its proximal end, such as by screw threads 27, to a concentrically mounted hollow barrel cam 25 disposed within the handle assembly. The distal end of the inner shaft terminates in a linkage assembly 28, shown in FIGS. 1, 6, 7, and 8, for operating the surgical attachment. The linkage assembly is actuated by a pushrod 30 that extends entirely through the inner shaft and the barrel cam, can be moved axially reciprocally relative thereto, and is operably connected to the handle assembly 14 in a manner described below.

The linkage assembly is best seen in FIGS. 1 and 6 through 8 and comprises two linkages 32 and a cam link 34 that is secured to the distal end of pushrod 30. One linkage 32 is provided for each jaw member 9 of the surgical attachment and includes a pushrod pin 36, an arcuate slot 38 and an engaging pin 40 as shown in FIG. 8. (For simplicity of illustration, only one linkage and one jaw are shown in FIGS. 7 and 8.) The pushrod pin 36 fits in a linear slot 42 in cam link 34 and the arcuate slot 38 receives a pin 44 on the cam link. The cam link is sandwiched between two identical linkages when assembled and thus has a pin 44 on each side for engaging the arcuate slots of the respective linkages. Each jaw member 9 includes a lever arm 15 having a pinhole 17 for receiving engaging pin 40 from one of the linkages and a pivot hole 19. A linkage housing 29 secured to the distal end of the inner shaft 18 houses the linkages and the cam link and pivotally supports the jaw members 9 by means of a screw 21 projecting through the pivot holes 19 in each jaw member.

When the pushrod is retracted to its rest position, the jaws 9 are open as shown in FIGS. 6 and 7. In this position the linkages 32 are angled outwardly from the linkage assembly. As the pushrod is urged distally by operation of the handle assembly, the pins 44 on the cam link 34 slide forwardly in each arcuate slot 38 and cam the linkages inwardly about the sliding pushrod pin 36. By this motion, the pins 40 on the linkages interacting with the lever arms 15 through engagement with the pinholes 17 force the jaws to pivot toward each other about the screw 21, which acts as a fulcrum, and to close tightly. In accordance with the present invention, the pins 44 are integrally formed, for example, by being machined on the cam link and the pins 36 and 40 are integrally formed, for example, by being machined on the linkages. By providing integrally machined pins, as opposed to separate pins riveted to the cam link and linkages, greater strength and durability in the linkage assembly can be achieved.

Figure 9:
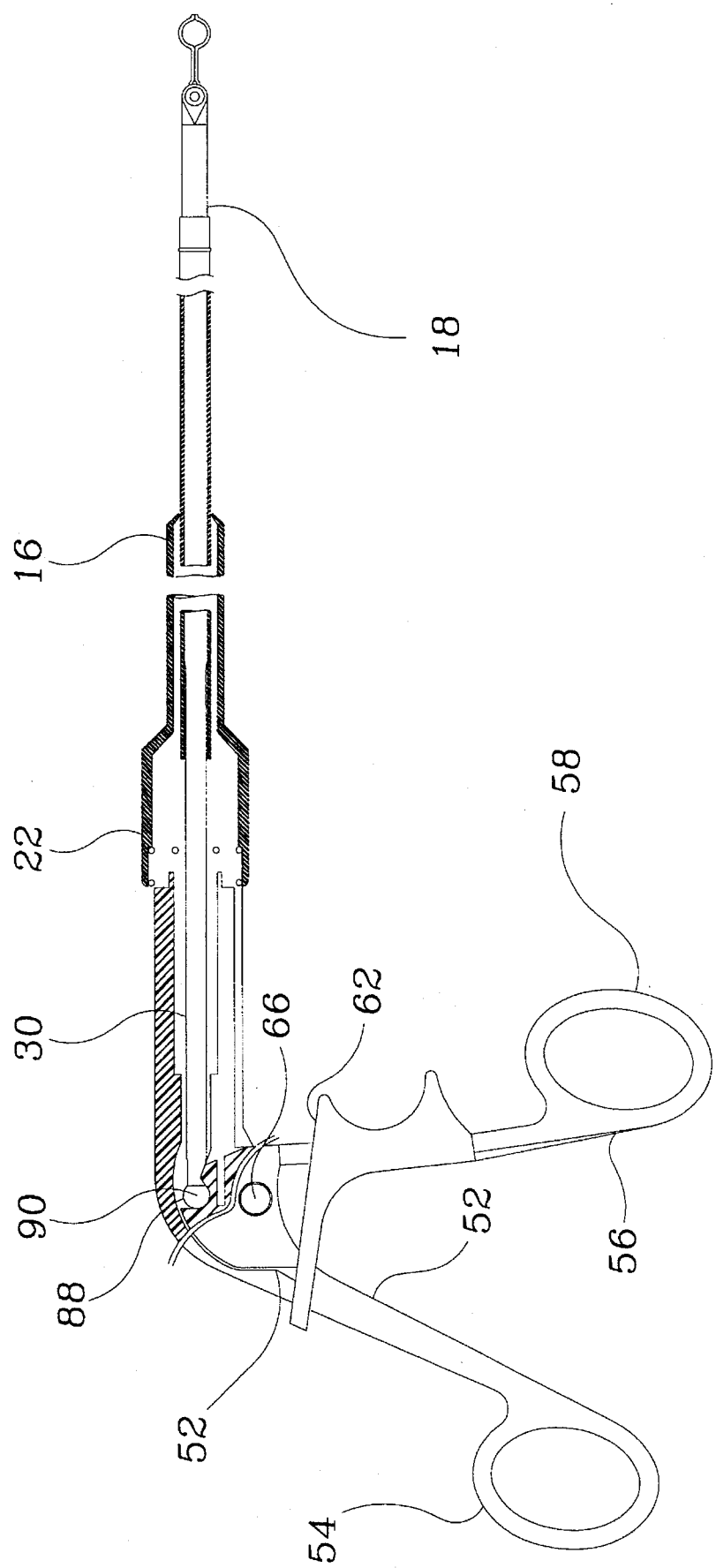
FIG. 9 is a side elevational view of the endoscopic surgical instrument of the present invention with the attached surgical tool in the closed-jaw position.

The handle assembly 14 is shown generally in FIG. 1 and comprises a scissors-like actuating mechanism 50 with a stationary leg 52 terminating in a thumb loop 54 and a pivoting leg 56 terminating in a finger loop 58. The pivoting leg is operably connected to the pushrod 30 and pivots about a pivot pin 60 when squeezed by the surgeon/user to axially slide the pushrod and actuate the linkage assembly. A locking slide control 62 has a channel 63 (shown in phantom lines in FIG. 1) for sliding along the pivoting leg and includes an open finger loop 64 for easy manipulation by the finger of the user. The slide control has a rear end portion 68 that fits over and embraces the stationary leg 52. The rear end portion includes slide control ridges 70 for engaging complimentary ridges 72 on the back surface of the stationary leg, which are shown in FIG. 2. In this manner, when the pivoting leg 56 is squeezed to actuate the pushrod 30, the locking slide control 62 can be lowered as shown in FIG. 9 to engage the slide control ridges 70 with the stationary leg ridges 72 and prevent the pivoting leg from returning to its rest position. The actuated jaws can thus be locked in a closed position. As FIG. 9 also illustrates, the stationary leg 52 includes a contoured portion 53 for abutting the pivoting leg 56 and limiting its movement about the pivot pin 60. The contoured portion thus prevents overtravel of the jaws.

FIGS. 6, 7 and 10 further provide an internal view of the handle assembly. As shown there, a notch 88 at the upper portion of the pivoting leg 56 receives and secures therein a spherical portion 90 at the proximal end of the pushrod 30. The spherical portion is able to rotate within the notch, in the fashion of a ball and socket joint, when the pushrod is rotated about its axis as will be discussed below. In this manner, the leg 56 pivots about pivot pin 60 when squeezed and forces pushrod in the distal, or forward, direction to actuate the linkage assembly and close the attached surgical tool. When the squeezing pressure on the leg 56 is released, the leg is biased back to its rest position by the force of a compressed coil spring 91 disposed within the handle assembly.

The barrel cam 25 secured to the inner shaft is supported at its proximal end in a body 76 of the handle assembly by a bushing 93, such as a TEFLON® bearing, disposed in a seat of the body. The distal end of the barrel cam is supported by a transition ring 95 and a spanner nut 97. The barrel cam has a helical groove 94 on its outer surface. An open finger loop slide control mechanism 74 is slidably engaged to the handle assembly and operates a cam driver 96 that projects into the helical groove. As the slide control slides axially, the cam driver runs in the helical groove 94 and causes the barrel cam to rotate about its longitudinal axis. The rotating barrel cam in turn rotates the connected inner shaft, the linkage assembly, and the surgical tool attached thereto. The pushrod also rotates about its longitudinal axis upon rotation of the barrel cam, which is permitted by the ball and socket connection of the notch 88 and spherical portion 90. The pitch of the helical groove 94 can be chosen to regulate the degree of rotation of the barrel cam based on the amount of linear movement of slide control mechanism 74. The slide control mechanism and barrel cam assembly can thus provide very fine rotational resolution for precisely orienting the surgical jaws. As will be appreciated, the outer shaft does not rotate as the jaws are oriented by rotational movement of the inner shaft. Thus, the outer shaft 16 does not move relative to the cannula and an airtight seal therebetween can be maintained.

When the handle assembly is in the rest, or open, position or is being actuated, the slide control mechanism 74 can be freely manipulated to orient the jaws. However, the surgical instrument is designed to restrain or inhibit rotation of the barrel cam, and thus the jaws, when the handle assembly is fully actuated and gripping tissue. The state of being fully actuated is achieved when the jaws are completely closed or closed around the object to be gripped to the point where the jaws cannot be further closed.

More specifically, as best seen in FIG. 10, which provides the most detailed and enlarged view of the handle assembly and flushport system, a distal end of the barrel cam 25 includes a flange 110 secured to the barrel cam. The flange is positioned immediately adjacent a proximal end of the stationary spanner nut 97 and, when the handle assembly is at rest or is being actuated, i.e., when there is no gripping force on the jaws, rotates freely with the barrel cam when linear movement is imparted to slide control mechanism 74. However, when the jaws are fully actuated, the distally-directed axial force on the pushrod supplied by squeezing the pivoting leg 56 of the handle assembly is transferred through the cam link 34 and the linkages 32 to exert a small axial force on linkage housing 29. This axial force on the linkage housing actually pulls the attached inner shaft and connected barrel cam slightly in the distal direction an amount sufficient to cause contact between the flange 110 and the proximal end of the spanner nut. The contact between these elements creates a friction force which inhibits or at least restrains the ability of the barrel cam to rotate.

A multiple flush port system 78 is disposed at the distal end of handle assembly body 76 for cleaning and providing improved sterilizability of the instrument. As best seen in FIGS. 2 and 10, the flushing system includes a transition ring 95, or stepped cylindrical collar, having a first cylindrical portion 80 having a distal flush port 82 and a second, larger cylindrical portion 84 with a proximal flush port 86. Both distal and proximal flush ports accept cleansing fluid from a male luer, such as a 10 cc syringe, for flushing out tissue and fluid after each use of the surgical instrument.

The distal and proximal flush ports of the multiple flush port system are concealed during use by the back end 22 of the outer shaft to minimize exposure to foreign fluids or matter. As shown, for example, in FIG. 10, first and second elastomeric O-rings 90 and 92 provide a secure fit between the transition ring and the back end 22 of outer shaft 16. A first sealing ring 99 is positioned between the transition ring 95 and the barrel cam 25, and a second sealing ring 101 is positioned between the pushrod 30 and the barrel cam and abuts a flared portion 103 of the pushrod. The sealing rings are made of TEFLON®, for example, and are designed to provide an air-tight seal between fluid passages leading from each respective flush port while permitting relative movement between the pushrod 30 and an interior surface of the barrel cam. The flared portion acts to seal the fluid passages leading from the distal and proximal flush ports from each other, and also prevents pneumoperitoneal loss in the insufflated body cavity.

To clean the surgical instrument, the outer shaft slides axially toward the stop 26 on the inner shaft to expose the distal and proximal flush ports 82 and 86 as shown in FIG. 2. The barrel cam provides two sets of holes for receiving the cleansing fluid dispersed through the flush ports. A first set of holes 100 and 102 align with the flush ports 86 and 82, respectively, when the slide control mechanism 74 is in its rearwardmost position, as shown in FIG. 10, and a second set of holes 104 and 106 align with the flush ports when the slide control is positioned fully forwardly. The flush ports receive the cleansing fluid from the male luer such as a 10cc syringe. The distal flush port 82 receives the cleansing fluid for flushing the pushrod 30 and the linkage assembly 28. The proximal port 86 receives cleansing fluid for flushing the cam barrel 25 and other components within the handle assembly body 76. Also, the barrel cam may be provided with circumferential grooves to allow cleansing fluids to flow into holes 100 and 102 regardless of the rotational positions of the flush ports 86 and 82.

Accordingly, it will be appreciated that the present invention provides e novel endoscopic surgical instrument that can be reliably sealed in an cannula to maintain body cavity insufflation. The operative elements of the instrument, such as tissue gripping jaws, may be rotated easily about the elongated axis of the device to be properly oriented at any time during the surgical procedure, all without disturbing the air-tight seal between the instrument and the cannula. Nevertheless, such rotation of the operative elements is restrained when they are fully actuated. For these and other reasons described above in detail, the present invention provides substantial improvements over know endoscopic surgical instruments of this type.

Although specific embodiments of the present invention have been described above in detail, it will be understood that this description is merely for purposes of illustration. Various modifications of and equivalent structures corresponding to the disclosed aspects of the preferred embodiment in addition to those described above may be made by those skilled in the art without departing from the spirit of the present invention which is defined in the following claims, the scope of which is to be accorded the broadest interpretation so as to encompass such modifications and equivalent structures.

What is claimed is:

1. An endoscopic surgical instrument, comprising:

an elongated shaft assembly having an outer shaft and an inner shaft disposed within said outer shaft;

a handle assembly connected to a proximal end of said shaft assembly;

first actuation means, connected to said handle assembly, for actuating a surgical tool operably connected to a distal end of said inner shaft; and second actuation means for rotating said inner shaft within said outer shaft to orient the surgical tool with respect to an axial direction of said shaft assembly, said second actuation means connected to said handle assembly, wherein said second actuation means includes a barrel cam connected to said inner shaft and having a helical groove, and a control mechanism with a cam driver engaging the helical groove, and wherein said control mechanism is mounted for linear movement with said handle assembly thereby to convert such linear movement into rotary motion of said inner shaft by interaction of the helical groove and said cam driver.

2. An endoscopic surgical instrument according to claim 1, wherein said first actuation means includes a pushrod axially reciprocally disposed within said inner shaft and having a proximal end connected to said handle assembly.

3. An endoscopic surgical instrument according to claim 2, further comprising a linkage assembly connected to a distal end of said inner shaft and including linkages connected to a distal end of said pushrod, said linkage assembly being actuated by axial sliding movement of said pushrod.

4. An endoscopic surgical instrument according to claim 1, further comprising means, located proximate to said barrel cam, for restraining rotation of said inner shaft when said first actuation means is fully actuated to operate said surgical tool.

5. An endoscopic surgical instrument according to claim 1, wherein said first actuation means includes a stationary leg and a pivoting leg pivotally connected to said stationary leg, with said pivoting leg operably associated with said handle assembly.

6. An endoscopic surgical instrument according to claim 5, further comprising a locking mechanism mountable with said handle assembly for locking said pivoting leg in an actuated position relative to said stationary leg.

7. An endoscopic surgical instrument according to claim 5, wherein said stationary leg and said pivoting leg include limiting means for limiting movement of said pivoting leg relative to said stationary leg.

8. An endoscopic surgical instrument according to claim 1, wherein said handle assembly includes a transition ring at its distal end, said transition ring having means defining a flushing system including at least one flush port in said transition ring.

9. An endoscopic surgical instrument according to claim 8, wherein said outer shaft is axially slidably disposed on said inner shaft and includes an enlarged back end for concealing said flush port.

10. An endoscopic surgical instrument according to claim 9, wherein said inner shaft includes a stop for limiting axial sliding movement of said outer shaft.

11. An endoscopic surgical instrument, comprising:
an elongated shaft assembly including an outer shaft, an inner shaft disposed within said outer shaft, and a pushrod disposed within said inner shaft;
a handle assembly connected to a proximal end of said elongated shaft, said handle assembly including an actuating mechanism for actuating said pushrod in the axial direction; and
means for imparting rotational movement to said inner shaft, wherein
said rotational movement imparting means includes a barrel cam having a helical groove and connected to a proximal end of said inner shaft, and further includes linear moving means, engagable with said barrel cam, for converting linear movement into rotational movement of said inner shaft.

12. An endoscopic surgical instrument according to claim 11, wherein said linear moving means includes a slide control slidably engaged with said handle assembly and having a cam driver engagable in the helical groove.

13. An endoscopic surgical instrument according to claim 11, further comprising means for restraining rotation of said barrel cam when said actuating mechanism is fully actuated, said restraining means located proximate to said barrel cam.

14. An endoscopic surgical instrument according to claim 11, wherein said actuating mechanism includes a stationary leg and a pivoting leg pivotally connected to said stationary leg and operably connected to said pushrod.

15. An endoscopic surgical instrument according to claim 14, further comprising a locking mechanism engagable with said actuating mechanism for locking said pivoting leg in an actuated position.

16. An endoscopic surgical instrument according to claim 14, wherein said stationary leg and said pivoting leg include limiting means for limiting movement of said pivoting leg relative to said stationary leg.

17. An endoscopic surgical instrument according to claim 11, wherein said handle assembly includes a transition ring at its distal end, said transition ring having means defining a flushing system including at least one flush port in said transition ring.

18. An endoscopic surgical instrument according to claim 17, wherein said outer shaft is axially slidably disposed on said inner shaft and includes an enlarged back end for concealing said flush port.

19. An endoscopic surgical instrument according to claim 18, wherein said inner shaft includes a stop for limiting axial movement of said outer shaft.

20. An endoscopic surgical instrument, comprising:
an elongated shaft assembly including an outer shaft, an inner shaft disposed within said outer shaft and a pushrod mounted within said inner shaft for movement in an axial direction; and
a handle assembly connected to a proximal end of said shaft assembly, said handle assembly including a pivoting leg operably connected to said pushrod, a hollow barrel cam connected to said inner shaft and having a helical groove, and a sliding control mechanism operably connected to said barrel cam and mounted on said handle assembly for linear movement, wherein linear movement of said control mechanism imparts rotational movement to said barrel cam and said inner shaft.

21. An endoscopic surgical instrument according to claim 20, wherein said control mechanism includes a finger loop mounted for linear movement with respect to said handle assembly and a cam driver engagable in the helical groove.

22. An endoscopic surgical instrument according to claim 20, further comprising a locking mechanism connected to said pivoting leg, said handle assembly further comprising a stationary leg, wherein said locking mechanism slides along said pivoting leg to engage said stationary leg and lock said pivoting leg in an actuated position.

23. An endoscopic surgical instrument according to claim 22, wherein said stationary leg and said pivoting leg include limiting means for limiting movement of said pivoting leg.

24. An endoscopic surgical instrument according to claim 23, further comprising a linkage assembly disposed at a distal end of said inner shaft and connected to said pushrod.

25. An endoscopic surgical instrument according to claim 24, wherein said linkage assembly includes a pair of linkages and a camming link sandwiched therebetween, said camming link connected to a distal end of said pushrod and said linkages being connectable to a surgical tool for actuation by axial movement of said pushrod.

26. An endoscopic surgical instrument according to claim 25, wherein each said linkage includes an integrally formed pin for engaging a straight slot in said camming link, and said camming link includes an integrally formed pin for engaging an arcuate slot in each said linkage.

27. An endoscopic surgical instrument according to claim 20, wherein said handle assembly includes a transition ring at its distal end, said transition ring having means for defining a flushing system including at least one flush port in said transition ring.

28. An endoscopic surgical instrument according to claim 27, wherein said outer shaft is mounted for axial movement on said inner shaft and includes an enlarged back end for concealing said flush port.

29. An endoscopic surgical instrument according to claim 28, wherein said inner shaft includes a stop for limiting axial movement of said outer shaft.

30. An endoscopic surgical instrument according to claim 20, further comprising means, located proximate to said barrel cam, for restraining rotation of said barrel cam when said handle assembly is fully actuated.

* * * * *